(12) United States Patent
Hong-Lin

(10) Patent No.: US 11,944,713 B2
(45) Date of Patent: Apr. 2, 2024

(54) BUTTON

(71) Applicant: Yen Hong-Lin, Taoyuan (TW)

(72) Inventor: Yen Hong-Lin, Taoyuan (TW)

(73) Assignee: Yen Hong-Lin, Taoyuan (TW)

( * ) Notice: Subject to any disclaimer, the term of this patent is extended or adjusted under 35 U.S.C. 154(b) by 452 days.

(21) Appl. No.: 17/408,559

(22) Filed: Aug. 23, 2021

(65) Prior Publication Data

US 2022/0054691 A1 Feb. 24, 2022

(30) Foreign Application Priority Data

Aug. 24, 2020 (TW) .................................. 109128816

(51) Int. Cl.
*A61L 2/26* (2006.01)
*A61L 2/10* (2006.01)
*F21V 23/04* (2006.01)
*G05G 1/02* (2006.01)

(52) U.S. Cl.
CPC ..................................... *A61L 2/26* (2013.01); *A61L 2/10* (2013.01); *F21V 23/04* (2013.01); *G05G 1/02* (2013.01); *A61L 2202/11* (2013.01); *A61L 2202/14* (2013.01)

(58) Field of Classification Search
CPC .......... A61L 2/26; A61L 2/10; A61L 2202/11; A61L 2202/14; A61L 2202/16; F21V 23/04; G05G 1/02

USPC ....................................... 250/453.11, 455.11
See application file for complete search history.

(56) References Cited

U.S. PATENT DOCUMENTS

| 5,651,450 | A | * | 7/1997 | Priesemuth | .......... | H01H 13/023 |
| | | | | | | 200/292 |
| 2016/0271280 | A1 | * | 9/2016 | Liao | ....................... | G06F 3/0393 |
| 2017/0224853 | A1 | * | 8/2017 | Jay | ............................. | A61L 2/26 |

* cited by examiner

*Primary Examiner* — Jason L McCormack
(74) *Attorney, Agent, or Firm* — Amin, Turocy & Watson, LLP

(57) ABSTRACT

The present inventive concept discloses a button which comprising a body, a lighting control unit and a cap. The body comprises a side wall and a base, wherein the side wall of the body is substantially disposed around and protrudes from the base to form a first accommodating space between the base and the side wall of the body; the lighting control unit is disposed in the first accommodating space, and the lighting control unit comprises a UV light-emitting element and a switch, wherein the switch is used for switching on/off the UV light-emitting element; and the cap comprises a side wall and a top, wherein the side wall of the cap is substantially disposed around and protrudes from the top to form a second accommodating space between the top and the side wall of the cap, and the top has a portion corresponding to a position irradiated by light beams of the UV light-emitting element is substantially made of a UV penetrable material, and wherein the cap separably covers at least one of the body or the lighting control unit.

14 Claims, 4 Drawing Sheets

BUTTON

RELATED APPLICATIONS

The present application claims the priority of Taiwan Application No. 109128816, filed on Aug. 24, 2020, the disclosure of which is hereby incorporated by reference herein in its entirety.

BACKGROUND OF THE INVENTION

1. Field of the Invention

The present disclosure generally relates to a button, particularly, to a button enabling to disinfect and sanitize itself and the surrounding by UV light.

2. Description of the Related Art

In order to improve the convenience, there are plenty of machines with different functions in our daily life, such as elevators, auto doors with buttons, vending machines, ticket vending machines, lights and so on. Most of these devices and equipments have elements, like buttons, which would be touched by users. Buttons on the devices and equipments are usually used by different users. Some users' body parts, like fingers, pressing the buttons or objects, like gloves, touching the buttons may carry pathogens, such as bacteria or viruses, which may affect public health. These buttons would become mediums for the bacteria or viruses. When diseases caused by such bacteria or viruses are outbreak, it is a very essential issue to clean and disinfect these buttons on the devices and equipments.

In order to clean the buttons, the buttons in the elevator could be refitted to be UV-infectious, i.e., ultraviolet light-emitting elements could be installed inside the buttons in the prior art. Whenever the buttons are used by users, the UV light-emitting elements would be driven to be turned on so as to clean and disinfect the buttons.

However, if the above-mentioned UV-infectious buttons were not equipped in the elevators while the elevator was installed, the original buttons have to be replaced by the UV-infectious buttons. This would increase the cost and cause inconvenience of management. Besides, buttons for different elevators may have their own shapes or structures. If the specification of the buttons does not match the requirement of the elevators, it would be difficult to replace the original buttons to the UV-infectious ones. Moreover, the above-mentioned UV-infectious buttons have to be installed and electrically connected to and powered by the power system of the elevators. Therefore, the UV-infectious buttons have to be installed and maintained by professional technicians.

In addition to using the UV-infectious buttons in the elevators, it depends on the designs of other devices or equipments if the UV-infectious buttons can be installed for those devices or equipments. In fact, the design is rarely seen in those devices or equipments. One of the main reasons is that not all buttons can be replaced independently or easily and this is why the UV-infectious buttons are not common.

Therefore, it is an urgent problem to be solved in this industry that how to provide a button capable of sanitizing and disinfection can be mobile and can be used by users easily.

SUMMARY OF THE INVENTION

In light of solving the foregoing problems of the prior art, the present inventive concept provides a button. The button comprises a body, a lighting control unit and a cap. The body comprises a side wall and a base, wherein the side wall of the body is substantially disposed around and protrudes from the base to form a first accommodating space between the base and the side wall of the body. The lighting control unit is disposed in the first accommodating space, and the lighting control unit comprises an ultraviolet light-emitting element (UV light-emitting element) and a switch, wherein the switch is used for switching on/off the UV light-emitting element. The cap comprises a side wall and a top, wherein the side wall of the cap is substantially disposed around and protrudes from the top to form a second accommodating space between the top and the side wall of the cap, and the top has a portion corresponding to a position irradiated by light beams of the UV light-emitting element is substantially made of a UV penetrable material, and wherein the cap separably covers at least one of the body or the lighting control unit.

In an embodiment of the present inventive concept, the top of the cap has a portion corresponding to the switch is substantially made of an elastic material.

In an embodiment of the present inventive concept, the side wall of the body has a first connection part located outside the side wall of the body and the side wall of the cap has a second connection part located inside the side wall of the cap, wherein the second connection part and the first connection part are connected to each other separably.

In an embodiment of the present inventive concept, the side wall of the body has a first connection part located inside the side wall of the body and the side wall of the cap has a second connection part located outside the side wall of the cap, wherein the second connection part and the first connection part are connected to each other separably.

In an embodiment of the present inventive concept, the base of the body or the side wall of the body further comprises a first locating part inside the base of the body or inside the side wall of the body and the lighting control unit further comprises a second locating part, wherein the second locating part and the first locating part joint to each other separably.

In an embodiment of the present inventive concept, the button further comprises an electric power unit which is electrically connected to the UV light-emitting element and the switch, and the electric power unit is used for supplying electric power required by the operation of the UV light-emitting element and the switch.

In an embodiment of the present inventive concept, the lighting control unit further comprises a fastening member, wherein the electric power unit is fastened to the lighting control unit by the fastening member.

In an embodiment of the present inventive concept, the base of the body or the side wall of the body further comprises a first locating part located inside the base of the body or inside the side wall of the body and the lighting control unit further comprises a second locating part, wherein the second locating part and the first locating part joint to each other separably, and wherein the second locating part is further a pin of the lighting control unit, which is used for electrically connected to a positive electrode terminal or a negative electrode terminal of the electric power unit.

In an embodiment of the present inventive concept, the button further comprises an adhesive member disposed outside the base of the body.

In an embodiment of the present inventive concept, the lighting control unit further comprises a timer module, wherein the timer module is electrically connected to the switch and used for controlling time cycle of the on/off state of the UV light-emitting element according a preset operation mode of the switch.

In an embodiment of the present inventive concept, the button further comprises an indicating member disposed inside or outside the top of the cap.

In an embodiment of the present inventive concept, wherein the base of the body further comprises a holding part disposed outside the base of the body.

In an embodiment of the present inventive concept, the side wall of the cap further comprises two through holes disposed outside the side wall of the cap and a preset spacing is between the two through holes.

In an embodiment of the present inventive concept, the side wall of the body further comprises a groove disposed outside the side wall of the body corresponding to a position where the two through holes are disposed outside the side wall of the cap.

Compared to the conventional prior art, users may press the top of the cap of the button of the present inventive concept to switch on the UV light-emitting element to emit UV light by the lighting control unit disposed in the body and the cap, so that the UV light may sanitize and disinfect the cap of the button. Moreover, the button could comprise an electric power unit. It is not necessary for the button of the present inventive concept to connect an external power supply. The button of the present inventive concept may function as a sole device and can be used anywhere and in any circumstances as required. The button of the present inventive concept may comprise an adhesive member and an indicating member. Users may attach the button of the present inventive concept to the original button, which would keep the function of the original button and provide a clean button to be pressed.

DETAILED DESCRIPTION

The present inventive concept is described by the following specific embodiments. Those with ordinary skills in the arts can readily understand other advantages and functions of the present inventive concept after reading the disclosure of this specification. Any changes or adjustments made to their relative relationships, without modifying the substantial technical contents, are also to be construed as within the range implementable by the present inventive concept.

Moreover, the word "exemplary" or "embodiment" is used herein to mean serving as an example, instance, or illustration. Any aspect or design described herein as exemplary or an embodiment is not necessarily to be construed as preferred or advantageous over other aspects or designs. Rather, use of the word "exemplary" or "embodiment" is intended to present concepts and techniques in a concrete fashion.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

Figure 1:
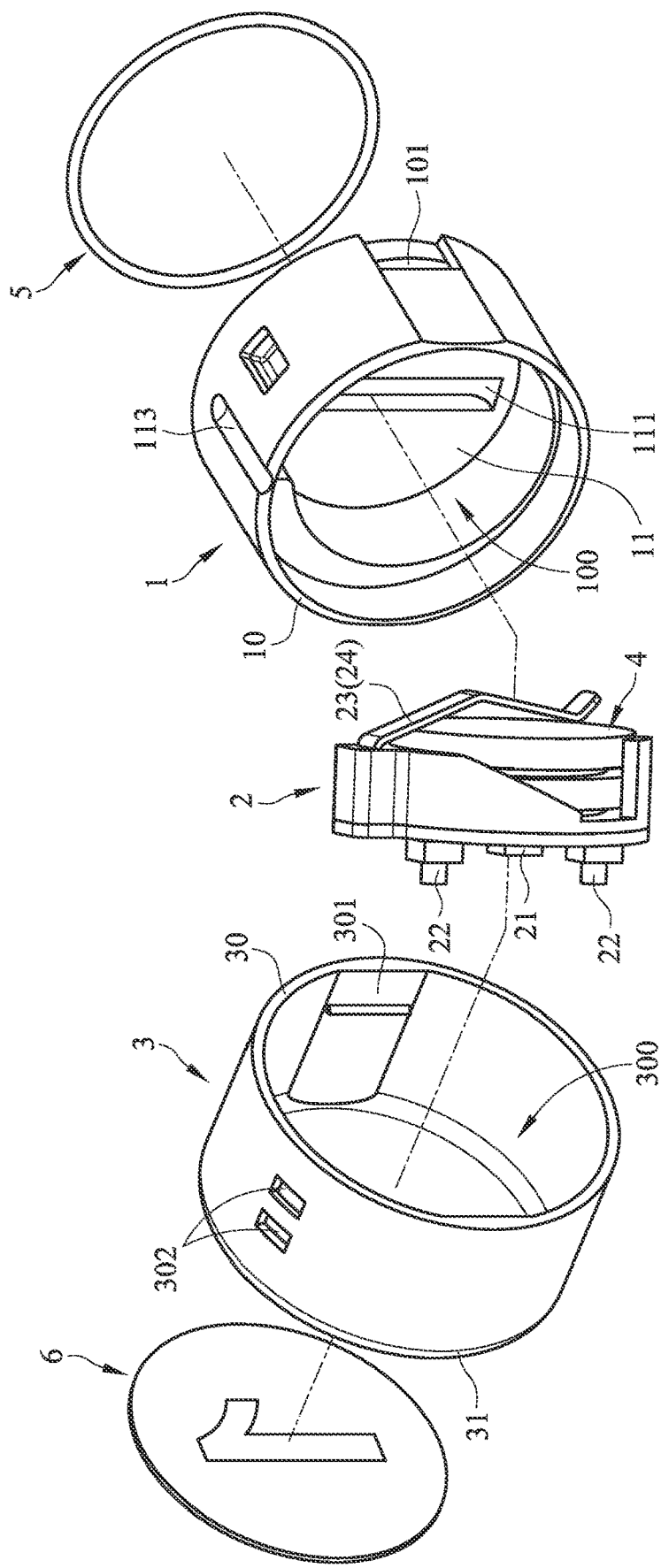
FIG. 1 is a parts breakdown schematic view of a button according to the present inventive concept.

Please refer to FIG. 1 which is a parts breakdown schematic view of a button according to the present inventive concept. As shown in FIG. 1, the button of the present inventive concept comprises a body 1, a lighting control unit 2 and a cap 3. The body 1 comprises a side wall 10 and a base 11, wherein the side wall 10 of the body 1 is substantially disposed around and protrudes from the base 11 to form a first accommodating space 100 between the base 11 and the side wall 10 of the body 1. The lighting control unit 2 may be disposed in the first accommodating space 100, and the lighting control unit 2 comprises an ultraviolet light-emitting element (UV light-emitting element) 21 and a switch 22, wherein the switch 22 is used for switching on/off the UV light-emitting element 21. The cap 3 comprises a side wall 30 and a top 31, wherein the side wall 30 of the cap 31 is substantially disposed around and protrudes from the top 31 to form a second accommodating space 300 between the top 31 and the side wall 30 of the cap 3, and the cap 3 separably covers at least one of the body 1 or the lighting control unit 2 in order to change or repair the lighting control unit 2 or any element connected to the lighting control unit 2.

In this embodiment, the internal cross section area surrounded by the side wall 30 of the cap 3 may be larger or substantially equal to the external cross section area surrounded by the side wall 10 of the body 1, so that the cap 3 separably covers the body 1 and the lighting control unit 2. In another embodiment, the internal cross section area surrounded by the side wall 30 of the cap 3 may be smaller or substantially equal to the external cross section area surrounded by the side wall 10 of the body 1, so that the cap 3 separably covers the lighting control unit 2 by the body 1 coupling to the cap 3.

In this embodiment, the top 31 has at least a portion corresponding to a position irradiated by light beams of the UV light-emitting element 21 is substantially made of a UV penetrable material, so that UV light emitted by the UV light-emitting element 21 may sanitize and disinfect the top 31 to reduce the amount of bacteria or viruses on the top 31.

Figure 2A:
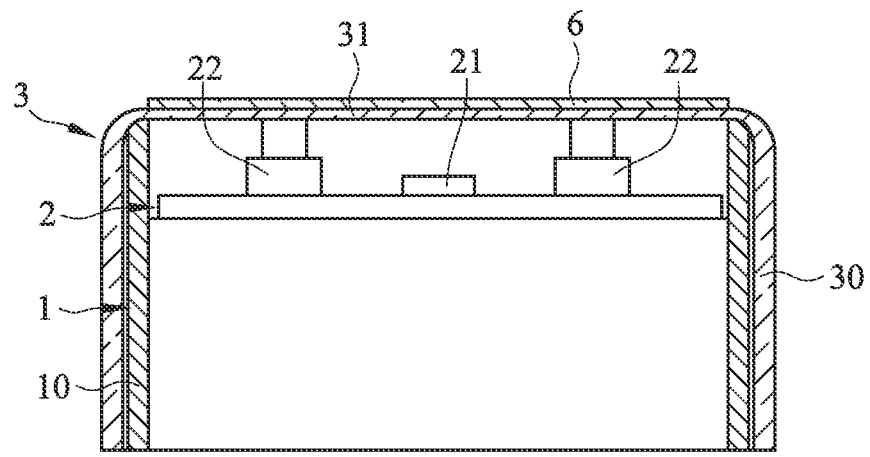
FIGS. 2A and 2B are section views of a button according to the present inventive concept in use.
Figure 2B:
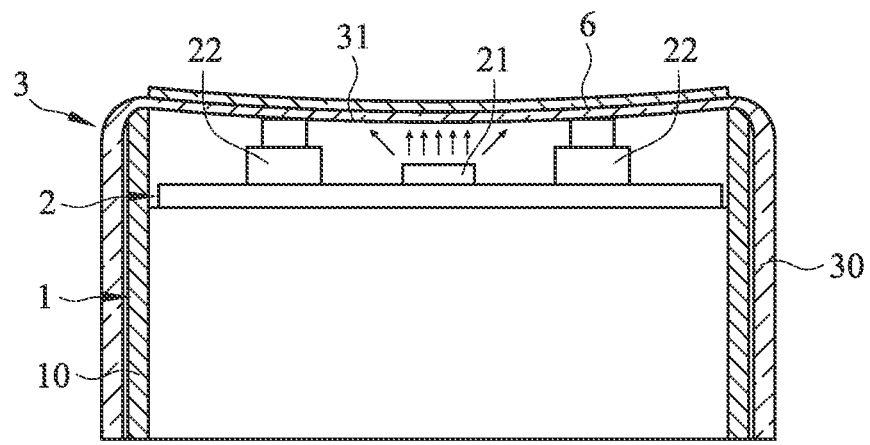

In an embodiment of the present inventive concept, the top 31 of the cap 3 has at least a portion corresponding to the switch 22 may be substantially made of an elastic material. The elastic material may be, but not limited to, for example plastics, resins or silicone, such as PP, PE, PC, PS, ABS, PA(Nylon), thermoplastic Elastomer (TPE) or thermoplastic Polyurethane (TPU) or the like. When the body 1, the lighting control unit 2 and the cap 3 are set together as shown in FIG. 2A, users may press the top 31 at the position corresponding to where the switch 22 is disposed as shown in FIG. 2B to switch on/off the switch 22, so that the UV light-emitting element may be turned on to emit UV light like the arrows shown in FIG. 2B or to be turned off. In this embodiment, preferably, the portion of the top 31 corresponding to where the switch 22 is disposed may has a thinness which may be about 0.5 mm, but not limited to it. The thickness may be adjusted by the chosen materials, the predetermined feels of the rebound for the button and/or the requirement of mistouch prevention.

Please further refer to FIG. 1. The internal cross section area surrounded by the side wall 30 of the cap 3 may be larger or substantially equal to the external cross section area surrounded by the side wall 10 of the body 1, so that the cap 3 may separably cover the body 1 and the lighting control unit 2. In this embodiment, preferably, the side wall 10 of the body 1 may have a first connection part 101 located outside the side wall 10 of the body 1 and the side wall 30 of the cap 3 may have a second connection part 301 located inside the side wall 30 of the cap 3, wherein the second connection part 301 and the first connection part 101 may be connected to each other separably.

The internal cross section area surrounded by the side wall 30 of the cap 3 may be smaller or substantially equal to the external cross section area surrounded by the side wall 10 of the body 1, so that the cap 3 separably covers the lighting control unit 2 by the body 1 coupling to the cap 3. In this embodiment, the first connection part 101 may be located inside the side wall 10 of the body 1 and correspondingly the second connection part 301 may be located outside the side wall 30 of the cap 3, and the second connection part 301 and the first connection part 101 may be connected to each other separably (not shown in the figures).

As shown in FIG. 1, in an embodiment of the present inventive concept, the base 11 of the body 1 may further comprise a first locating part 111 inside the base 11 of the body 1 and the lighting control unit 2 may further comprise a second locating part 23, wherein the second locating part 23 and the first locating part 111 may joint to each other separably. By the structures of the first locating part 111 and the second locating part 23, users may dispose the lighting control unit 2 properly at the base 11 of the body 1 easily and prevent the lighting control unit 2 being moved unwillingly in use. In another embodiment of the present inventive concept, the first locating part 111 may be disposed inside the side wall 10 of the body 1 and the lighting control unit 2 may further comprise a second locating part 23 disposed at the position corresponding to the first locating part 111 (not shown in the figures).

As shown in FIG. 1, in an embodiment of the present inventive concept, the button may further comprise an electric power unit 4. The electric power unit 4 may be electrically connected to the UV light-emitting element 21 and the switch 22. The electric power unit 4 may be used for supplying electric power required by the operation of the UV light-emitting element 21 and the switch 22. In another embodiment of the present inventive concept, preferably, the lighting control unit 2 may further comprise a fastening member 24, wherein the electric power unit 4 may be fastened to the lighting control unit 2 by the fastening member 24. More preferably, the base 11 of the body 1 may further comprise a first locating part 111 located inside the base 11 of the body 1 and the lighting control unit 2 may further comprise a second locating part 23, wherein the second locating part 23 and the first locating part 111 may joint to each other separably. In this embodiment, the second locating part 23 may further be a pin of the lighting control unit 2 which is used for electrically connected to a positive electrode terminal or a negative electrode terminal of the electric power unit 4. In this embodiment, the second locating part 23 may be, for example, a conductive metal spring contact, but not limited to. In other words, the second locating part 23 may be used for conducting electric current and jointing to the first locating part 111.

Please further refer to FIG. 1. The button of the present inventive concept may further comprise an adhesive member 5. The adhesive member 5 may be disposed outside the base of the body. Preferably, the adhesive member 5 may be, for example, transparent or non-transparent glue or tape.

Figure 3:
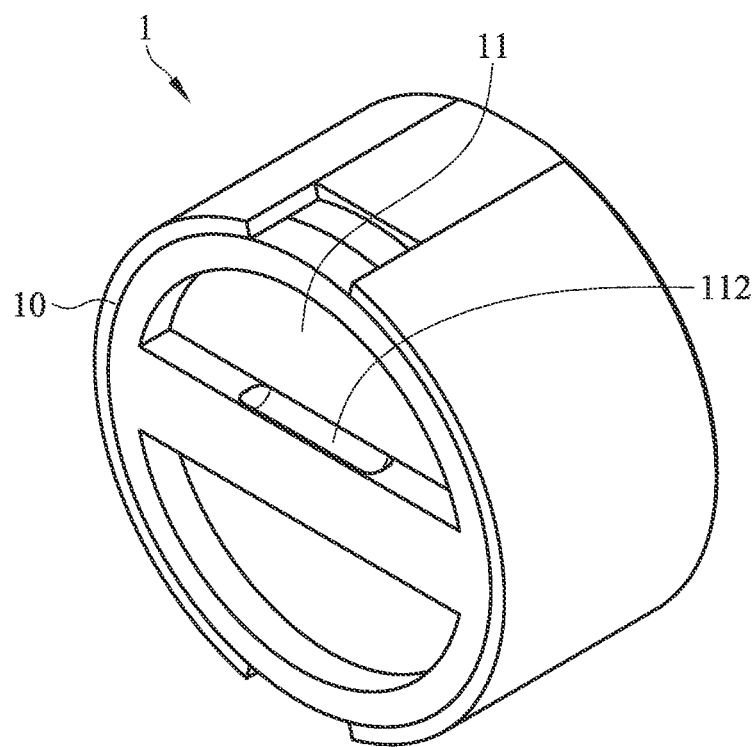
FIG. 3 is a structure schematic view of a button according to the present inventive concept.

Please refer to FIG. 3. In an embodiment of the present inventive concept, the base 11 of the body 1 may further comprise a holding part 112. As shown in FIG. 3, the holding part 1 may be a strip structure disposed outside the base 11 of the body 1 and there is a groove in the middle of the two sides of the strip structure for users to hold to separate the combined cap 3 and body 1.

Please refer to FIG. 1 again. In an embodiment of the present inventive concept, the side wall 30 of the cap 3 may further comprise two through holes 302 disposed outside the side wall 30 of the cap 3 with a preset spacing between the two through holes 302. In this embodiment, a sling or a rope may be disposed through the two through holes 302 for users to carry the button of the present inventive concept easily. Preferably, the side wall 10 of the body 1 may further comprise a groove 113 disposed outside the side wall 10 of the body 1 corresponding to a position where the two through holes 302 are disposed outside the side wall 30 of the cap 3 to accommodate the knot in the sling or the rope at the two through holes 302.

Figure 4:
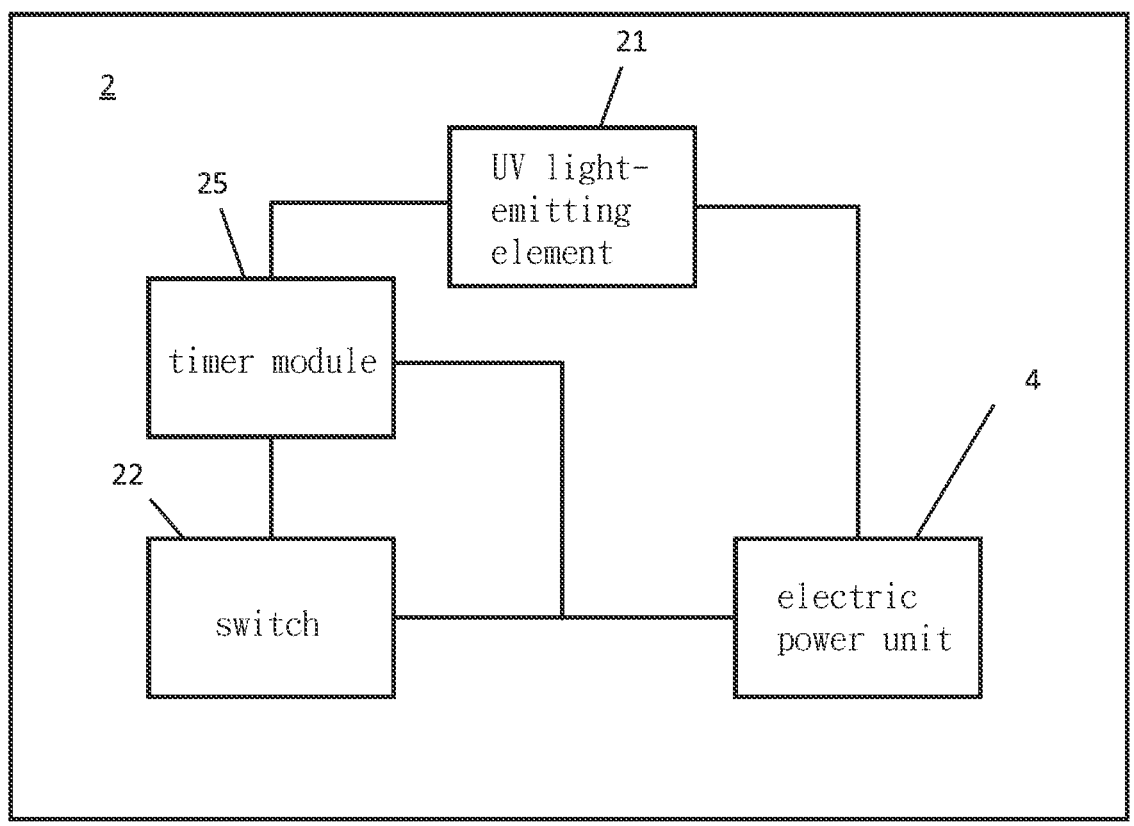
FIG. 4 is a block diagram of the elements of a button according to the present inventive concept.

Please refer to FIG. 4. In an embodiment of the present inventive concept, the lighting control unit 2 may further comprise a timer module 25. The timer module 25 may be electrically connected to the switch 22 and used for controlling time cycle of the on/off state of the UV light-emitting element 21 according a preset operation mode of the switch 22. In an embodiment, the preset time circle may be that the UV light-emitting element 21 turn on for 5 seconds by users pressing the switch 22 once to disinfect the cap 3. Alternatively, the preset time circle may be that the UV light-emitting element 21 turn on for 20 seconds by users pressing the switch 22 twice to disinfect any object.

Please refer to FIG. 1 again. In another embodiment, the button of the present inventive concept may further comprise an indicating member 6. The indicating member 6 may be disposed inside or outside the top 31 of the cap 3. In an embodiment, the indicating member 6 may be, for example, self-adhesive or electrostatic adhesive and any required numbers, texts or symbols may be printed on the indicating member.

As describe above, in another embodiment, the button of the present inventive concept may be equipped with the indicating member 6 printed with numbers of floors or texts, such as open/close and stuck on the original button of an elevator. When users press the button of the present inventive concept to operate the elevator, the UV light-emitting element 21 would turn on to sanitize and disinfect the top 31 of the cap 3 for a certain time to prevent the spread of viruses and bacteria by the button.

In summary, the button of the present inventive concept comprises a lighting control unit in the body and the cap. Users may press the top of the cap of the button of the present inventive concept to turn on the UV light-emitting element of the lighting control unit, so that the emitted UV light may sanitize and disinfect the top of the cap. Moreover, the button could comprise an electric power unit, so it is not necessary for the button of the present inventive concept to connect an external power supply. The button of the present inventive concept may function as a sole device and can be used anywhere and in any circumstances as required. The button of the present inventive concept may comprise an adhesive member and an indicating member. Users may attach the button of the present inventive concept to the original button, which would maintain the function of the original button and provide a clean button to be pressed.

The foregoing descriptions of the detailed embodiments are only illustrated to disclose the features and functions of the present inventive concept and not restrictive of the scope of the present inventive concept. It should be understood to those in the art that all modifications and variations according to the spirit and principle in the disclosure of the present inventive concept should fall within the scope of the appended claims.

What is claimed is:

1. A button, comprising:
a body, comprising a side wall and a base, wherein the side wall of the body is substantially disposed around and protrudes from the base to form a first accommodating space between the base and the side wall of the body;
a lighting control unit, disposed in the first accommodating space, and the lighting control unit comprises an ultraviolet light-emitting element (UV light-emitting element) and a switch, wherein the switch is used for switching on/off the UV light-emitting element; and
a cap, comprising a side wall and a top, wherein the side wall of the cap is substantially disposed around and protrudes from the top to form a second accommodating space between the top and the side wall of the cap, and the top has a portion corresponding to a position irradiated by light beams of the UV light-emitting element is substantially made of a UV penetrable material, and wherein the cap separably covers at least one of the body or the lighting control unit.

2. The button of claim 1, wherein the top of the cap has a portion corresponding to the switch is substantially made of an elastic material.

3. The button of claim 1, wherein the side wall of the body has a first connection part located outside the side wall of the body and the side wall of the cap has a second connection part located inside the side wall of the cap, wherein the second connection part and the first connection part are connected to each other separably.

4. The button of claim 1, wherein the side wall of the body has a first connection part located inside the side wall of the body and the side wall of the cap has a second connection part located outside the side wall of the cap, wherein the second connection part and the first connection part are connected to each other separably.

5. The button of claim 1, wherein the base of the body or the side wall of the body further comprises a first locating part inside the base of the body or inside the side wall of the body and the lighting control unit further comprises a second locating part, wherein the second locating part and the first locating part joint to each other separably.

6. The button of claim 1, further comprising an electric power unit which is electrically connected to the UV light-emitting element and the switch, and the electric power unit is used for supplying electric power required by the operation of the UV light-emitting element and the switch.

7. The button of claim 6, wherein the lighting control unit further comprises a fastening member, wherein the electric power unit is fastened to the lighting control unit by the fastening member.

8. The button of claim 6, wherein the base of the body or the side wall of the body further comprises a first locating part located inside the base of the body or inside the side wall of the body and the lighting control unit further comprises a second locating part, wherein the second locating part and the first locating part joint to each other separably, and wherein the second locating part is further a pin of the lighting control unit, which is used for electrically connected to a positive electrode terminal or a negative electrode terminal of the electric power unit.

9. The button of claim 1, further comprising an adhesive member disposed outside the base of the body.

10. The button of claim 1, wherein the lighting control unit further comprises a timer module, wherein the timer module is electrically connected to the switch and used for controlling time cycle of the on/off state of the UV light-emitting element according a preset operation mode of the switch.

11. The button of claim 1, further comprising an indicating member disposed inside or outside the top of the cap.

12. The button of claim 1, wherein the base of the body further comprises a holding part disposed outside the base of the body.

13. The button of claim 1, wherein the side wall of the cap further comprises two through holes disposed outside the side wall of the cap and a preset spacing is between the two through holes.

14. The button of claim 13, wherein the side wall of the body further comprises a groove disposed outside the side wall of the body corresponding to a position where the two through holes are disposed outside the side wall of the cap.

* * * * *